United States Patent [19]

Soloway et al.

[11] Patent Number: 4,782,169

[45] Date of Patent: Nov. 1, 1988

[54] 4,7-DIOXATRICYCLO(3.2.1.0$^{3,6}$)OCTANE ETHER

[75] Inventors: Samuel B. Soloway, Modesto, Calif.; Pierre Vogel, Preverenges; Claude H. Aubin Le Drian, Lausanne, both of Switzerland; James E. Powell, Ripon, Calif.

[73] Assignee: E. I. Du Pont de Nemours and Company, Wilmington, Del.

[21] Appl. No.: 916,334

[22] Filed: Oct. 6, 1986

[51] Int. Cl.$^4$ .............................. C07D 493/18
[52] U.S. Cl. .................... 549/459; 549/60; 549/414; 549/216; 546/22; 546/167; 546/152; 546/270; 548/336; 548/256; 548/262; 548/134; 548/136; 548/526; 548/374; 548/235; 548/247; 548/202
[58] Field of Search ............ 549/459, 60, 414, 216; 546/22, 167, 152, 270; 548/336, 256, 262, 134, 136, 526, 374, 235, 247, 202

[56] References Cited

U.S. PATENT DOCUMENTS

| | | | |
|---|---|---|---|
| 4,486,220 | 12/1984 | Payne et al. | 71/92 |
| 4,525,203 | 6/1985 | Payne et al. | 71/88 |
| 4,567,283 | 1/1986 | Payne et al. | 549/546 |
| 4,670,041 | 6/1987 | Payne et al. | 546/270 |

FOREIGN PATENT DOCUMENTS 2188931 4/1987 United Kingdom .

OTHER PUBLICATIONS

Vieira et al., *Helvetica Chimica Acta*, 65(6): 1700–06 (1982).
Vieira et al., *Helvetica Chimica Acta*, 66(6): 1865–71 (1983).
Black et al., *Helvetica Chimica Acta*, 67: 1612–15 (1984).
*J. Amer. Chem. Soc. Perkin Trans. I*, 903–906 (1985).
*J. Amer. Chem. Soc.*, vol. 5, 4115–4125 (1962).
*Aust. J. Chem.*, vol. 36, 2473–2482 (1983).

*Primary Examiner*—Jane T. Fan

[57] ABSTRACT

Compounds of the Formula I, II, III, VI and VII

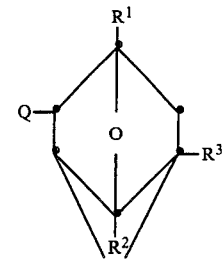

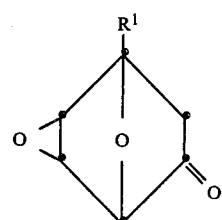

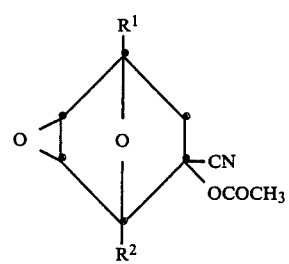

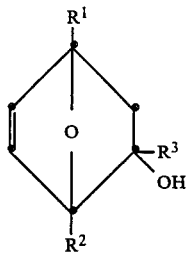

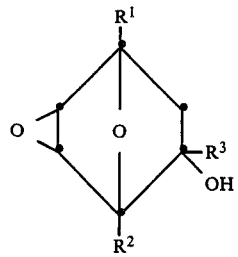

wherein the symbols have defined meanings are herbicides, plant growth regulators or intermediates thereof.

8 Claims, No Drawings

4,7-DIOXATRICYCLO(3.2.1.0^{3,6})OCTANE ETHER

FIELD OF THE INVENTION

The present invention relates to novel ether derivatives, their use as herbicides and plant growth regulators, to compositions containing these ether derivatives for these uses and to certain novel intermediates to the ether derivatives.

SUMMARY OF THE INVENTION

The present invention is directed to novel compounds of Formula I

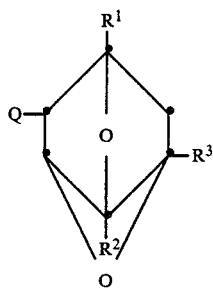

wherein $R^1$ is a hydrogen atom or a straight-chain alkyl group containing 1 to 4 carbon atoms, $R^2$ is hydrogen, an alkyl group containing 1 to 4 carbon atoms or a cycloalkyl group containing 3 to 6 carbon atoms; $R^3$ is a hydrogen atom, an alkyl group containing 1 to 6 carbon atoms, a cycloalkyl group containing 3 to 6 carbon atoms, an alkenyl or alkynyl group containing 2 to 4 carbon atoms, a phenyl group optionally substituted by one or more of chlorine, fluorine or methyl, tetrahydro-2H-pyran-2-yl, pyridinyl, pyridinylmethyl, mono- or bis(alkoxycarbonyl)methyl in which each alkyl group contains 1 to 4 carbon atoms, mono- or bis(hydroxycarbonyl)methyl, mono- or dicyanomethyl, cyano, dihydroxyphosphinyl, dialkoxyphosphinyl or dialkylphosphinyl in which each alkyl group contains 1 to 4 carbon atoms, alkylthio or alkylsulfonyl in which each alkyl group contains 1 to 4 carbon atoms, arylthio or arylsulfonyl in which each aryl contains 6 to 10 ring carbon atoms in a monocyclic or fused bicyclic aromatic ring, or acylamino in which the acyl group contains 1 to 4 carbon atoms, and Q is OH or the group OCH$_2$R in which R is an optionally substituted unsaturated hydrocarbon group containing 2 to 4 carbon atoms, an aromatic group containing up to 14 carbon atoms, a heterocyclic group in which the one or two heteroatoms are each selected from O, S or N and containing up to 14 carbon atoms or N-oxide or acid addition salt of an N-heterocyclic group; a cyano group; a cycloalkenyl group containing 5 to 7 carbon atoms; a cycloalkyl group containing 3 to 10 carbon atoms; and stereoisomeric forms or mixtures thereof.

The compounds of Formula I of the invention when Q is OCH$_2$R have been found useful for influencing plant growth and controlling the growth of unwanted plants, being particularly active with respect to grassy weeds. For example, the compounds can change plant morphology; depress the growth of plants, such as broadleafed weeds; inhibit germination; or totally or selectively kill plants depending on the amount used.

Optional substituents in R include hydroxy; cyano; halogen atoms having an atomic number of from 9 to 35, inclusive; alkyl, optionally substituted by hydroxy, amino, (alkylcarbonyl)amino, alkoxy or alkylthio; haloalkyl, alkoxy, haloalkoxy, alkylthio, haloalkylthio, alkylsulfinyl, alkylsulfonyl, alkenyl or alkynyl of up to 4 carbon atoms; carboxyl; aminocarbonyl, amino, or (alkylcarbonyl)amino, each of which hydrogen attached to nitrogen can be substituted by alkyl of 1 to 4 carbon atoms; or equivalent kinds of substituents. Preferably, the optional substituent is an alkyl group containing 1 or 2 carbon atoms, especially a methyl group.

Compounds that possess substantially the same plant growth regulator or herbicidal utility as those described above and can be prepared in like manner are equivalents thereof and include compounds wherein, for example, R is an optionally-substituted, unsaturated hydrocarbyl, mono- or polycyclic aromatic, or saturated or unsaturated cycloalkyl or heterocyclic moiety, or the like, or equivalents thereof, including but not limited to allyl, propargyl, cyclopropyl, 1-methylcyclopropyl, phenyl, naphthyl, imidazolyl, triazolyl, thiadiazolyl, 2-quinolinyl, 1-isoquinolinyl, pyrrolyl, cyclohexenyl, N-methylimidazolyl, N-methylpyrazolyl, isoxazolyl, oxazolyl, isothiazolyl, thiazolyl, thienyl, 5-methyl-2-furanyl, tetrahydro-2-pyranyl and the like.

Non-limiting illustrative species of the invention include those compounds of Formula I set out below

| Q | $R^1$ | $R^2$ | $R^3$ |
|---|---|---|---|
| 2-methylbenzyloxy | $C_2H_5$ | $C_2H_5$ | H |
| 2-methylbenzyloxy | $C_2H_5$ | $C_2H_5$ | methyl |
| 2-methylbenzyloxy | $C_2H_5$ | $C_2H_5$ | ethyl |
| 2-methylbenzyloxy | $C_2H_5$ | $C_2H_5$ | phenyl |
| 2-methylbenzyloxy | $C_2H_5$ | $C_2H_5$ | ethynyl |
| 2-methylbenzyloxy | $CH_3$ | $CH_3$ | H |
| 2-methylbenzyloxy | $CH_3$ | $CH_3$ | methyl |
| 2-methylbenzyloxy | $CH_3$ | $CH_3$ | ethyl |
| 2-methylbenzyloxy | $CH_3$ | $CH_3$ | phenyl |
| 2-methylbenzyloxy | $CH_3$ | $CH_3$ | ethynyl |
| 2-fluorobenzyloxy | $CH_3$ | $i$-$C_3H_5$ | H |
| 2,6-dichlorobenzyloxy | $CH_3$ | $CH_3$ | CN |
| 2-fluorobenzyloxy | $C_2H_5$ | $C_2H_5$ | $CO_2H$ |
| (3-chloro-2-thienyl)methoxy | $CH_3$ | $CH_3$ | phenyl |
| (6-chloro-2-pyridinyl)methoxy | $C_2H_5$ | $C_2H_5$ | dimethoxyphosphinyl |
| tetrahydro-2-pyranylmethoxy | H | $C_2H_5$ | acetylamino |
| benzyloxy | $C_2H_5$ | $C_2H_5$ | pyridinyl |
| 2-methylbenzyloxy | $CH_3$ | sec-$C_4H_7$ | methylthio |
| (1-cyclohexenyl)methoxy | $CH_3$ | $C_2H_5$ | phenylsulfonyl |
| 4-fluorobenzyloxy | H | H | bis(ethoxycarbonyl)methyl |
| 2-chlorobenzyloxy | $C_2H_5$ | $C_2H_5$ | allyl |
| 1-naphthylmethoxy | H | $CH_3$ | ethynyl |
| 2-furanylmethoxy | $CH_3$ | $CH_3$ | ethyl |
| propargyloxy | $CH_3$ | $CH_3$ | isopropyl |
| benzyloxy | $CH_3$ | $CH_3$ | dicyanomethyl |
| 2-fluorobenzyloxy | $CH_3$ | $CH_3$ | cyanomethyl |
| pyridin-2-ylmethoxy | $CH_3$ | $CH_3$ | (methoxycarbonyl)methyl |
| 2-chlorobenzyloxy | $CH_3$ | $CH_3$ | carboxymethyl |
| cyclopropylmethoxy | $C_2H_5$ | $C_2H_5$ | tetrahydro-2H—pyran-2-yl | and the corresponding compounds of Formulas II, III, VI and VII.

In one embodiment of the compounds of Formula I, R is an ethynyl group; a phenyl group optionally substituted by one or two halogen atoms of atomic number 9 of 17 or by a methyl group; or a 5- or 6-membered heterocyclic group containing one or two heteroatoms of O, S or N, optionally ring-substituted on a carbon atom by halogen of atomic number 9 or 17 or by alkyl containing 1 or 2 carbon atoms. Preferably, R is phenyl, 2,6-difluorophenyl, 2,6-dichlorophenyl, 2-methylphenyl, 2-fluorophenyl, tetrahydro-2-pyranyl, 2-pyridinyl, 6-chloro-2-pyridinyl or 3-chloro-2-thienyl.

In another embodiment of the compounds of Formula I, $R^1$, $R^2$ and $R^3$ each independently is a hydrogen atom or an alkyl group containing 1 or 2 carbon atoms, e.g. methyl or ethyl. Preferably, $R^1$ and $R^2$ each is methyl or ethyl, especially methyl, and $R^3$ is hydrogen, methyl or ethyl.

As stated above, the invention includes N-oxides and salts of the compounds of Formula I in which R is an N-heterocyclic group. A salt is an acid addition salt or a quaternary ammonium salt, for example a compound of the general formula

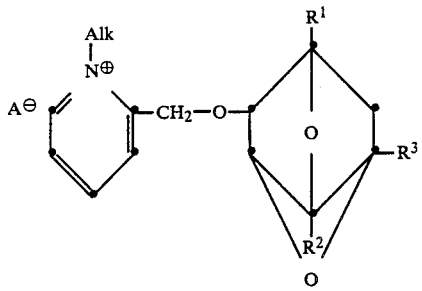

in which Alk represents an alkyl group having up to 6 carbon atoms, especially a methyl or an ethyl group, and $A^\ominus$ represents one equivalent of an anion, especially a halogen ion, for example an iodide or chloride ion, or one equivalent of a sulfate ion. From the halides, other salts can be prepared by known methods, such as the nitrate, sulfate, trifluoromethanesulfonate, acetate, borate, tartrate, succinate, phosphate, etc.

The compounds of Formula I exhibit geometrical and optical isomerism and may be prepared in geometrical and/or optically active forms, and as racemates. The various individual optical and geometrical forms, and various combinations thereof, of the compounds of Formula I usually have some difference in herbicidal or plant growth regulant properties. The present invention contemplates all the herbicidally or plant growth regulant active forms and useful novel intermediates resulting from synthesis, or deliberately created mixtures, or any isomer forms intermediate thereto. The ethers wherein the $RCH_2O$ group is cis to the oxygen atom bridging the 1,4-positions of the six-membered carbon ring are usually more active in regard to plants.

The compounds of Formula I of the invention wherein Q is $OCH_2R$ are prepared by treating the corresponding alcohols of Formula I wherein Q is OH or alcoholate thereof, with a compound of the formula $RCH_2X$ in which X is a halogen atom, such as bromine, chlorine or iodine, or is a mesyloxy, tosyloxy group or the like, preferably in the presence of a strong base and an inert diluent. The strong base is suitably an alkali metal hydride, hydroxide or carbonate, including, for example, sodium hydride, sodium hydroxide, potassium carbonate and the like, or organic bases, such as tertiary amines and ammonium compounds, for example, triethylamine, and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

The compounds $RCH_2X$ are generally known in the art, including U.S. Pat. Nos. 4,525,203, 4,542,244, 4,515,618 or the like.

The compounds of Formula I of the invention wherein Q is OH are prepared from the exo-dioxa (oxygen atoms cis with respect to six-membered carbon ring) ketone of Formula II

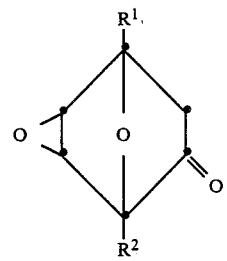

wherein $R^1$ and $R^2$ are as defined above, by treatment with nucleophiles corresponding to the moieties defined by $R^3$ in Formula I. For those nucleophiles containing an ester function subsequent saponification produces the corresponding acids.

The compounds of Formula II, which are novel and form part of this invention, are made by saponification, preferably in the presence of formaldehyde, of the compounds of Formula III, which are also novel and form part of this invention.

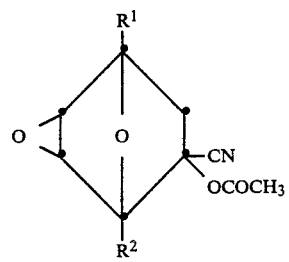

Compounds of Formula III are made by epoxidation, with a peroxy acid such as meta-chloroperbenzoic acid or the like, of the Diels-Alder adducts of Formula IV.

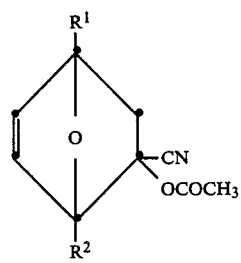

Compounds of Formula IV are generally known in the art and prepared as described in the literature; see E. Vieira and P. Vogel, *Helv. Chim. Acta.*, 65(6), pages 1700–1706 (1982). In compounds of formulas II, III, and IV, $R^1$ and $R^2$ are as defined for Formula I.

Compounds of Formula I, wherein Q is OH and $R^3$ is hydrogen, an alkyl group containing 1 to 6 carbon atoms, a cycloalkyl group containing 3 to 6 carbon atoms, an alkenyl or alkynyl group containing 2 to 4 carbon atoms, or phenyl optionally substituted by one or more of chlorine, fluorine, or methyl, tetrahydro-2H-pyran-2-yl, pyridinyl, pyridinylmethyl, mono- or bis-(alkoxycarbonyl)methyl in which each alkyl group contains 1 to 4 carbon atoms, mono- or bis-(hydroxycarbonyl)methyl, mono- or dicyanomethyl, dihydroxyphosphinyl, dialkoxyphosphinyl or dialkylphosphinyl in which each alkyl group contains 1 to 4 carbon atoms, are also prepared from compounds of Formula IV by an alternative sequence. Compounds of Formula IV are saponified by conventional means to afford compounds of Formula V, which are generally known in the art and prepared as described in the literature (see above citation).

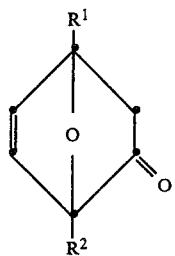

V

Compounds of Formula V are then treated with nucleophiles corresponding to the moieties defined by $R^3$ immediately above to afford compounds of Formula VI

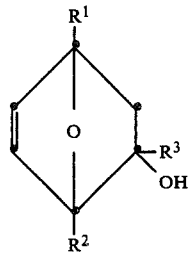

VI wherein $R^3$ is defined immediately above. The compounds of Formula VI, which are novel and form part of this invention, are epoxidized by conventional methods to produce compounds of Formula VII, which are also novel and form part of this invention, wherein $R^3$ is defined immediately above.

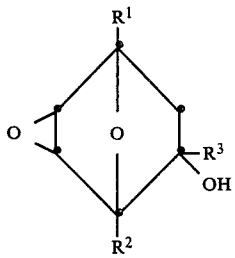

VII

Treatment of compounds of Formula VII with strong base, such as alkali metal hydroxides or alkoxides, affords compounds of Formula I wherein Q is OH.

Compounds of Formula II can also be prepared by conventional epoxidation of compounds of Formula V.

The compounds of Formula I are prepared by conventional methods as substantially pure enantiomers from the substantially pure enantiomers of Formulas IV or V, generally known in the art and prepared as described in the literature (E. Vieira and P. Vogel, *Helv. Chim. Acta.*, 66, pages 1865–1871 (1983) and K. A. Black and P. Vogel, ibid., 67, pages 1612–1615 (1984)) by the methods described above. Alternatively, compounds of Formula I can be prepared as substantially pure enantiomers by classical resolution of compounds of Formulas VI and VII and application of the methods described above to the resolved enantiomers. Compounds of Formula I wherein Q is OH can also be resolved by classical methods and the resulting enantiomers can be converted to the herbicidally active compounds of Formula I in substantially pure enantiomeric form.

In situations where the trans form for Q is OH in Formula I is desired, it can be obtained by oxidation of the 2-cis-hydroxy (as defined above) compound to the corresponding ketone followed by reduction of the ketone with sodium borohydride.

This invention is directed to novel chemical compounds of Formula I and their use in controlling (regulating) the natural growth or development of plants. In particular, this invention relates to the chemical treatment of plants to alter their natural growth or development for the purpose of enhancing various agricultural or horticultural features of the plants, and also to the control of undesirable vegetation, including killing.

This invention further relates to a method of controlling plant growth by controlling (regulating) the natural growth or development of plants comprising applying to said plants an effective, plant-regulating, non-lethal amount of the above compounds, as well as controlling undesirable vegetation comprising applying a herbicidally effective amount of the compounds to such vegetation.

As employed herein, the term "natural growth or development" designates the normal life cycle of a plant in accordance with its genetics and environment, in the absence of artificial external influences.

The term "regulating" is used herein to denote the bringing about through chemical means of any temporary or permanent modification or variation from the normal life cycle short of killing the plant.

With properly controlled application, a growth regulating effect can be achieved without herbicidal results. The amount which constitutes an effective amount varies not only with the particular material selected for treatment, but also with the regulatory effect to be achieved, the species of plant being treated and its stage of development, and whether a permanent or transient effect is sought.

Growth regulation may arise from the effect of the compound on either the physiological processes or the morphology of the plant, or from both in combination or in sequence. Morphological changes are generally noticeable by observable changes in the size, shape, color or texture of the treated plant or any of its parts like roots thereof, as well as in the quantity of fruit or flowers produced. Changes in physiological processes, on the other hand, occur within the treated plant and are usually hidden from the eye of an observer. Changes of this type most often occur in the production, location, storage or use of chemicals naturally occurring in the plant, such as hormones. Physiological changes may be visually detectable when followed by a change in morphology. In addition, numerous analytical procedures for determining the nature and magnitude of changes in the various physiological processes are known to those skilled in the art.

The active compounds of the instant invention serve to regulate the natural growth or development of treated plants, for example, crops such as soybeans, corn and the like, in a number of diverse ways, and it is to be understood that each compound may not produce identical regulatory effects on each plant species or at every rate of application. As stated above, responses will vary in accordance with the compound, the rate, the plant, etc.

The term "herbicidally effective amount" designates any amount of the compounds disclosed herein which will kill a plant or any portion thereof.

By "plants" is meant germinant seeds, emerging seedlings, and established vegetation, including roots and above-ground portions. Effects include killing, stunting or depression of growth, and inhibition of roots or the like. Herbicidal effects are generally achieved at higher application rates than growth regulating effects.

Certain Compounds of the Invention can exhibit geometrical and optical isomerism. The present invention includes all the biologically active compounds of Formula I of the invention and the useful novel intermediates and, thus it includes racemates and various geometric and/or optically-active isomers or mixtures enriched in such isomer forms which may be directly synthesized, resolved or mixed together. The various geometrical and optical isomers of the compounds of Formulas I and II may have different biological activity.

ILLUSTRATIVE EMBODIMENTS

The following illustrative embodiments should not be regarded as limiting the invention in any way. The products, including intermediates were identified by elemental, infrared, or nuclear magnetic resonance (NMR) spectral analyses as necessary.

EMBODIMENT 1

1,4-Dimethyl-7-oxabicyclo[2.2.1]hept-5-en-2-one

To a solution of 12 g of 2-cyano-2-acetoxy-1,4-dimethyl-7-oxabicyclo[2.2.1]hept-5-ene in 100 ml of methanol was added 0.028 mole of sodium methoxide. The mixture was stirred at room temperature for 3 hours, then 30 ml of formalin was added and the mixture was stirred an additional hour at room temperature. The reaction mixture was washed with 100 ml of water, then with 100 ml of saturated sodium chloride solution and extracted thrice with 100 ml of methylene chloride, dried ($Na_2SO_4$), concentrated and flash chromatographed using 1:1 hexane:methylene chloride as eluent to give 6 g of the desired product as a yellow oil.

EMBODIMENT 2

5,6-Epoxy-1,4-dimethyl-7-oxabicyclo[2.2.1]-heptan-2-one, exo-Isomer

To a stirred solution of 6.0 g of the oxo compound of Embodiment 1 above in 100 ml of methylene chloride was added 12.0 g of m-chloroperbenzoic acid at room temperature. After 3 days, the reaction mixture was filtered, and the filtrate was kept at 0° C. overnight, concentrated and flash chromatographed on silica gel with methylene chloride as eluent. Fractions 19–30 were combined and solvents removed to yield 5.0 g of the desired product as a yellow oil.

EMBODIMENT 3

1,6-Dimethyl-4,7-dioxatricyclo(3.2.1.0$^{3,6}$)-octan-2-ol, (1RS,2RS).

To a solution of 1.5 g of the epoxide of Embodiment 2 above in 10 ml of tetrahydrofuran under nitrogen was added dropwise at room temperature 5.5 ml of diisobutylaluminum hydride. The reaction mixture was stirred overnight, and then 40 ml of a solution of 35:5 water:acetic acid was added. The reaction mixture was extracted thrice with 100 ml methylene chloride, the combined methylene chloride extracts was dried ($Na_2SO_4$), the solvent was evaporated, and the residue was flash chromatographed with 8:2 methylene chloride:ethylacetate as eluent. The third fraction was treated to remove solvent to give 0.3 g of the desired product as a yellow oil.

EMBODIMENT 4

2-(Benzyloxy)-1,6-dimethyl-4,7-dioxatricyclo(3.2.1.0$^{3,6}$)octane, (1RS,2RS)

A solution of 0.2 g of the alcohol of Embodiment 3 in ether above was added to 80 mg of sodium hydride suspended in ether with evolution of hydrogen. After 1 hour at room temperature, 0.3 g of benzyl bromide was added, and the mixture was stirred overnight and heated at reflux for 2 hours. After cooling to room temperature, the mixture was poured into 20 ml of water, extracted thrice with 20 ml of methylene chloride, the methylene chloride extracts were dried ($Na_2SO_4$), the solvent was evaporated, and the residue flash chromatographed on silica gel with 8:2 methylene chloride:ethyl acetate as eluent. Fractions 6–14 were combined and after solvent evaporation gave 0.12 g of the desired product as a yellow oil.

EMBODIMENT 5

1-exo-2,4-Trimethyl-7-oxabicyclo[2.2.1]hept-5-en-endo-2-ol

To a solution of 3.45 g of the oxo compound of Embodiment 1 above in 10 ml of ether was added dropwise 2 ml of 2.9 molar methyl magnesium bromide in ether. The mixture was stirred overnight, 50 ml of water was added, the resulting mixture was extracted five times with methylene chloride, the combined methylene chloride extracts was dried, solvent was evaporated and the residue was flash chromatographed on silica gel with 8:2 methylene chloride:ethyl acetate. Fractions 14–30 were combined, and after solvent evaporation, gave 2.0 g of the desired product as a yellow oil.

EMBODIMENT 6

1-exo-2,4-Trimethyl-exo-5,6-epoxy-7-oxabicyclo[2.2.1]heptan-endo-2-ol

To a stirred solution of 1.54 g of the alcohol of Embodiment 5 above in 10 ml of methylene chloride was added 2.0 g of m-chloroperbenzoic acid. After 2 hours at room temperature the reaction mixture was filtered, and the filtrate was concentrated and flash chromatographed on silica gel with a methylene chloride-ethyl acetate solution as eluent. Fractions 14–40 were combined, and after solvent evaporation gave 1.2 g of the desired product as a white solid; m.p. 91°–92° C.

EMBODIMENT 7

1,5,6-Trimethyl-4,7-dioxatricyclo(3.2.1.0$^{3,6}$)octan-2-ol, (1RS,2RS)

To a mixture of 1 g of sodium hydroxide in 5 ml of water was added 1.0 g of the epoxy-alcohol of Embodiment 6 above. The reaction mixture was stirred overnight, neutralized with acetic acid, extracted thrice with 25 ml of methylene chloride. The organic layer was dried (Na$_2$SO$_4$) and flash chromatographed on silica gel with 7:3 methylene chloride:ethyl acetate as eluent. Fractions 10–32 were combined and after solvent evaporation, gave 0.7 g of the desired product as a clear oil.

EMBODIMENT 8

2-(Benzyloxy)-1,5,6-trimethyl-4,7-dioxatricyclo(3.2.1.0$^{3,6}$)octane, (1RS,2RS)

To a solution of 0.21 g of the alcohol of Embodiment 7 above in 5 ml of tetrahydrofuran was added 35 mg of sodium hydride with evolution of hydrogen. After 30 minutes at room temperature, 0.3 g of benzyl bromide was added. The reaction mixture was kept at room temperature overnight and, after 20 ml of water was added, extracted thrice with 25 ml of methylene chloride. The combined extracts was washed with 20 ml of saturated sodium chloride solution, dried (Na$_2$SO$_4$), evaporated, and flash-chromatographed with 9:1 methylene chloride:ethyl acetate. Fractions 16–24 were combined and, after solvent evaporation gave 0.21 g of the desired product as a yellow oil.

EMBODIMENT 9

1,5,6-Trimethyl-4,7-dioxatricyclo(3.2.1.0$^{3,6}$)octan-2-ol, (1RS,2RS)

A solution of 1.5 g of the oxo compound of Embodiment 2 above in 10 ml of ether was added to 2 ml of 2.9 molar methyl magnesium bromide in ether. The reaction mixture was stirred overnight at room temperature and, after 20 ml of water was added, extracted thrice with 25 ml of methylene chloride. The combined organic phases was dried (Na$_2$SO$_4$) and flash chromatographed on silica gel with 7:3 methylene chloride:ethyl acetate as eluent. Fractions 24–30 were combined and, after solvent evaporation, gave 0.26 g of the desired product as a thick oil.

EMBODIMENT 10

2-Cyano-2-acetoxy-exo-5,6-epoxy-7-oxabicyclo[2.2.1]heptane

2-Cyano-2-acetoxy-7-oxabicyclo[2.2.1]hept-5-ene, obtained by ZnI$_2$-catalyzed Diels-Alder addition of furan to 1-cyanovinyl acetate, was treated with m-chloroperbenzoic acid at 40° C. for 24 hours to give the desired epimeric products, isomer A, m.p. 117°–119° C. and isomer B, m.p. 174°–175° C.

EMBODIMENT 11 exo-5,6-Epoxy-7-oxabicyclo[2.2.1]heptan-2-one

The epoxides of Embodiment 10 above were treated with potassium carbonate and three equivalents formalin in aqueous methanol at 0° C. for 1 hour to give the desired oxo compound; m.p. 55°–56° C.

EMBODIMENT 12

4,7-Dioxatricyclo(3.2.1.0$^{3,6}$)octan-2-ol, (1RS,2RS)

A solution of the oxo compound of Embodiment 11 above in tetrahydrofuran was treated with one equivalent of diisobutylaluminum hydride at 20° C. to give the desired alcohol; m.p. 99°–101° C.

EMBODIMENT 13

2-(Benzyloxy)-4,7-dioxatricyclo(3.2.1.0$^{3,6}$)octane, (1RS,2RS)

Following procedures similar to those described in Embodiments 3 and 7 above, the desired product was obtained by treating the alcohol of Embodiment 12 above with benzyl bromide.

For application, a compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides—i.e., horticulturally acceptable carriers—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and- /or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants especially grassy weeds, is effected by applying a compound of Formula I, ordinarily in a composition of one of the aforementioned types, to soil in which the seeds of the unwanted plants are present, or to the foliage of the unwanted plants, especially grassy weeds and some broadleaf weeds. Some of the compounds can be selective to crops such as cotton, soybean, peanuts, wheat, rice and the like. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from about 0.01 to about 25 kg per hectare and preferably from about 0.1 to 10.0 kg per hectare of the compound of Formula I will be satisfactory.

The preemergence (soil) herbicidal activity of compounds of Formula I was evaluated by planting seeds of downy brome, johnsongrass, yellow foxtail, barnyardgrass, velvetleaf, morningglory, sicklepod and garden cress in test tubes, nominally measuring 25×200 millimeters, filled about three-quarters full of untreated soil, in each case covered on top with about 2.5 cubic centimeters of soil treated with 0.1 milligram of the test compound, to give a dosage of 2.0 pounds of test compound per acre. The seeds were planted on top of the treated soil and covered with about 1.5 cubic centimeters of untreated soil. The planted soil was held under a controlled regimen of temperature, moisture, and light. At 10 days, the amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

TABLE 1

| Compound No. | PREEMERGENCE HERBICIDAL ACTIVITY | | | | | | | |
|---|---|---|---|---|---|---|---|---|
| | DOBR | JOGR | YEFT | BYGR | VELE | MOGL | SIPO | GACR |
| 4 | 6 | 6 | 8 | 9 | 7 | 0 | 4 | 0 |
| 7 | 8 | 8 | 8 | 8 | 4 | 2 | 6 | 3 |

What is claimed is:

1. A compound of the Formula I

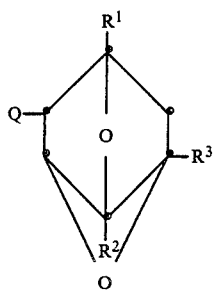

wherein $R^1$ is a hydrogen atom or a straight-chain alkyl group containing 1 to 4 carbon atoms; $R^2$ is a hydrogen atom, an alkyl group containing 1 to 4 carbon atoms or a cycloalkyl group containing 3 to 6 carbon atoms; $R^3$ is a hydrogen atom, an alkyl group containing 1 to 6 carbon atoms, a cycloalkyl group containing 3 to 6 carbon atoms, an alkenyl or alkynyl group containing 2 to 4 carbon atoms, a phenyl group optionally substituted by one or more of chlorine, fluorine or methyl, tetrahydro-2H-pyran-2-yl, pyridinyl, pyridinylmethyl, mono- or bis(alkoxycarbonyl)methyl in which each alkyl group contains 1 to 4 carbon atoms, mono- or bis(hydroxycarbonyl)methyl, mono- or dicyanomethyl, cyano, dihydroxyphosphinyl, dialkoxyphosphinyl or dialkylphosphinyl in which each alkyl group contains 1 to 4 carbon atoms, alkylthio or alkylsulfonyl in which each alkyl group contains 1 to 4 carbon atoms, arylthio or arylsulfonyl in which each aryl contains 6 to 10 ring carbon atoms in a monocyclic or fused bicyclic aromatic ring, or acylamino in which the acyl group contains 1 to 4 carbon atoms, and Q is OH or the group $OCH_2R$ in which R is an optionally substituted unsaturated hydrocarbon group containing 2 to 4 carbon atoms; an aromatic group containing up to 14 carbon atoms, a heterocyclic group consisting of imidazolyl, triazolyl, thiadiazolyl, quinolinyl, isoquinolinyl, pyrrolyl, pyrazolyl, isoxazolyl, oxazolyl, isothiazolyl, thiazolyl, thienyl, furanyl, tetrahydropyranyl and pyridinyl, or N-oxide or acid addition salt of an N-heterocyclic group, a cyano group, a cycloalkenyl group containing 5 to 7 carbon atoms, or a cycloalkyl group containing 3 to 10 carbon atoms; and stereoisomeric forms or mixtures thereof.

2. A compound according to claim 1 wherein R is an ethynyl group; a phenyl group optionally substituted by one or two halogen atoms of atomic number 9 or 17 or by a methyl group; or imidazolyl, triazolyl, pyrrolyl, isoxazolyl, oxazolyl, isothiazolyl, thiazolyl, thienyl, furanyl, tetrahydropyranyl, optionally ring substituted on a carbon atom by halogen of atomic number 9 or 17 or by alkyl containing 1 or 2 carbon atoms.

3. A compound according to claim 2 wherein $R^1$, $R^2$ and $R^3$ each independently is a hydrogen atom or an alkyl group containing 1 or 2 carbon atoms.

4. A compound according to claim 3 wherein $R^3$ is a methyl group.

5. A compound according to claim 4 wherein $R^1$ and $R^2$ are methyl or ethyl.

6. A compound according to claim 5 wherein R is phenyl, 2,6-difluorophenyl, 2,6-dichlorophenyl, 2-methylphenyl, 2-fluorophenyl, tetrahydro-2-pyranyl, 6-chloro-2-pyridinyl, 2-pyridinyl or 3-chloro-2-thienyl.

7. A compound according to claim 6 wherein $R^1$ and $R^2$ is methyl.

8. A compound according to claim 7 wherein R is phenyl.

* * * * *